(12) United States Patent
Taylor

(10) Patent No.: US 6,267,724 B1
(45) Date of Patent: Jul. 31, 2001

(54) IMPLANTABLE DIAGNOSTIC SENSOR

(75) Inventor: David W. Taylor, Dallas, TX (US)

(73) Assignee: MicroFab Technologies, Inc., Plano, TX (US)

( * ) Notice: Subject to any disclaimer, the term of this patent is extended or adjusted under 35 U.S.C. 154(b) by 0 days.

(21) Appl. No.: 09/364,717

(22) Filed: Jul. 30, 1999

Related U.S. Application Data

(60) Provisional application No. 60/094,648, filed on Jul. 30, 1998.

(51) Int. Cl.[7] .................................................. A61B 5/00
(52) U.S. Cl. ............................................. 600/309; 128/898
(58) Field of Search .................................. 600/309, 310, 600/322; 128/897, 898

(56) References Cited

U.S. PATENT DOCUMENTS 5,342,789  8/1994  Chick et al. .
5,494,030  2/1996  Swartz et al. .
5,706,805  1/1998  Swartz et al. .

*Primary Examiner*—Eric F. Winakur
(74) *Attorney, Agent, or Firm*—Locke Liddell & Sapp LLP

(57) ABSTRACT

A method of using an implantable diagnostic sensor capable of detecting a biologically relevant state or change in state of a human or animal subject. The method includes selecting a dynamic probe to produce a measurable change over a range of changes in responses to a varying biologically relevant state. The method also includes selecting a reference material capable of exhibiting a measurable state within the range of changes of the dynamic probe material that represents a desired response level of the dynamic probe material with respect to the biologically relevant state. Further, the method requires tattooing the probe material into the human or animal skin for comparing the state of the dynamic probe to the reference material.

8 Claims, 1 Drawing Sheet

IMPLANTABLE DIAGNOSTIC SENSOR

CROSS REFERENCE TO RELATED APPLICATION

This application is entitled to the benefit of provisional patent application Ser. No. 60/094,648 filed Jul. 30, 1998.

TECHNICAL FIELD OF THE INVENTION

This invention relates to implantation of diagnostic tattoos, specifically to a method to continuously and non-invasively monitor a wide array of parameters for both humans and animals. More particularly, the present invention relates to a tattooing method that allows assessment or monitoring of some biologically relevant state or change, including, but not limited to glucose levels, pathogen response chemicals such as interleukin, cytokine and immunoglobulin, temperature, pH, or any condition in which the molecules present in the interstitial fluid of the dermis change and can be monitored. Also covered in this patent are "temporary tattoos" which differ from tattoos in that they are implanted only in the epidermal layer, and thus are subject to wearing off through normal skin processes.

BACKGROUND OF THE INVENTION

Monitoring various biological body parameters is known. For example, diabetics find out their glucose level by pricking themselves several times per day The most common prior art involves taking body fluid samples, most commonly blood, and often sending them to a lab for analysis. Another common method is to expose test patches to a fluid sample, commonly urine. Urine testing has the advantage of not needing an invasive procedure like with blood. It has the limitation, however, of reflecting a cumulative average over hours where blood samples reflect the current state.

The prior art in regards to glucose involves puncturing the skin and collecting a small sample to be analyzed by the patient. This is an especially important case of prior art for two reasons. One reason is the number of tests performed per day is in the millions. Another important aspect of this test is that it typically needs to be and is done entirely by the patient with equipment that can be carried around in a purse or briefcase.

There are many diagnostic tools on the market with yield a visible change to indicate a condition or state of the body. Examples would include home pregnancy tests, pH strips, urine protein sticks, etc. While these are good demonstrations of instant readout of an important physiologic parameter, none of these are done as an implant.

The examples that follow include a glucose tattoo. It is based on the chemistry disclosed in U.S Pat. No. 5,342,789. In this patent there is a reference to tattooing in claim 21. It says "the method of claim 5 wherein said specific binding pair is tattooed into the skin of the individual". Claims 5 describes the relevant chemistry as being " . . . comprising of a specific binding pair which comprises a first member which is a glucose-binding ligand labeled with a first light absorbing material and a second member which is a glyco-conjugate labeled with a second light absorbing material . . .". It also claims " . . . placing a sensor in communication with glucose present in the body fluids of the individual in such a way that once in place said sensor does not exit the skin of the individual . . ." Nowhere in the patent does the means to accomplish this receive attention. How to accomplish this is an aim of this patent, The idea of an implanted sensor does not necessarily mean a dermal implant. Nowhere in the patent is there discussion of making particles suitable for tattooing.

Other patents pertaining to diagnostic tattoos are U.S. Pat. No. 5,494,030, "Apparatus and Methodology for Determining Oxygen in Biological Systems", and U.S. Pat. No. 5,706,805, "Apparatus and Methodology for Determining Oxygen Tension in Biological Systems". The '805 Patent is very specific to using EPR (electron paramagnetic resonance) in conjunction with carbon particles for oximetry measurements. The '030 Patent is directed solely at oxygen tension measurements using EPR and India ink. The '805 Patent broadens these claims to include a totally non-invasive approach using India ink or lithium phthalocyanine. It also mentions measuring free radicals, pH and temperature as possibilities using their EPR techniques.

This invention will allow the implantation of a diagnostic tattoo. The said tattoo would allow for continuous, noninvasive monitoring of a wide array of relevant parameters. The benefits of this invention are numerous. They include continuous monitoring capability, virtually any analyte that is present in interstitial fluid may be monitored, once implanted, readings are non-invasive and therefore no risk of infection, are extremely simple to read and understand, immune to contamination problems associate with fluid sample containers and sample acquisition techniques, and works equally well for the unconscious.

SUMMARY OF THE INVENTION

This invention will allow the implantation of a diagnostic tattoo. Said would allow continuous, noninvasive monitoring of a wide array of relevant parameters. For example, diabetics find out their glucose level without the need to prick themselves. The current technology requires them to prick themselves several times a day. If the indicator would reveal certain cytokine levels it could indicate the presence of a pathogen. For a war fighter it could alert him to biological warfare. The current proposed arts involve creating an array of spots that will each respond to a specific pathogen. If the war fighter is exposed to a new or mutated pathogen the array will not detect it. Since this tattoo would respond to the immune system, there would be no specificity to a particular pathogen and no limit to the pathogens which are detectable. If the tattoo were to be read by a photodetector, an alert message could be sent automatically to a base camp monitor that could be monitoring a large number of war fighters.

The diagnostic tattoo, involves creating an array of spots, each responding to a specific pathogen. The method is capable of detecting a biologically relevant state or change in state of a human or animal subject. This method includes selecting a dynamic probe material that produces a measurable change of state over a range of changes in response to a varying biologically relevant state in a human or animal subject. Additionally, the method consists of selecting a reference material that exhibits a measurable state within the range of changes of the dynamic probe material that represents a desired response level of the dynamic probe material with respect to the biologically relevant state. The invention also consists of tattooing the dynamic probe material into the skin of the subject and tattooing the reference material for comparison next to the tattooed dynamic probe material in the skin of the subject and comparing the state of the dynamic probe material to the state of the reference material to ascertain a biologically relevant state of the subject for which the probe was selected.

The diagnostic system will consist of implanted particles that are coated with probes. A person skilled in the art will be able to coal the particles will little or at most routine experimentation. The probes will monitor the surrounding extra cellular fluid by direct contact or in-flow to the interior of the particle. A person skilled in the art of tattooing would be able to implant a suspension of the particles into the correct layer of the skin.

According to an embodiment of the invention, tattoo patterning could be employed in order to facilitate high resolution and accuracy in reading the tattoo, for example, by having a round spot of dynamic particles surrounded by a ring of static particles. The user could then compare the difference in color to determine whether a reaction has occurred.

According to another preferred embodiment of the invention, a second format of patterning for the invention could be a segmented plus non segmented type. The simplest case would be a bar of one type along side a sequence of segments. If the dynamic portion of the tattoo were to change gradually over a range, then the upper bar would be made from dynamic particles and the lower segments would be made from static particles.

According to another preferred embodiment of the invention, a step would be used to show sharp transitions at different values. These transitions would look like on/off indicators.

According to yet another embodiment of the invention, the tattoo would be made from dynamic particles shaped as numbers corresponding to the specific probe response.

DETAILED DESCRIPTION OF THE INVENTION

This invention relates to a method of using diagnostic tattoos. A "tattoo" is defined as any pattern of particles implanted in the dermal layer of the skin. The term "diagnostic" is used to denote the particles possession of a chemical or chemicals ("probe molecules" or "probes") that allow assessment of some biologically relevant state or change. The tattoo may include both "static" and "dynamic" particles, where static is defined as particles that do not change and dynamic is defined as particles that do change in response to a change in some parameter. This change may or may not be reversible.

The diagnostic system will consist of implanted particles, which will not cause an immune reaction themselves. These particles will contain or be coated with probes, which can easily be performed by a person skilled in the art of coating particles, such as the staff at molecular Probes in Eugene, Oregon or Polysciences in Warrington, Pa. They would be able to coat the particles with little or at most routine experimentation. While they are in the business of coating stock sphere sizes with any of the 1200 or so probes shown in their catalog, they can also coat other probes onto other particles. The probes will monitor the surrounding extra-cellular fluid by direct contact or in-flow to the interior of the particle.

Figure 1:
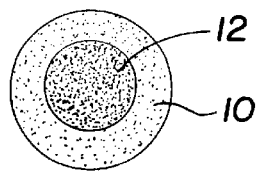
FIG. 1 is a representation of the tattoo having a static and dynamic portion in concentric circles.

Another important element of this invention is patterning. Tattoo patterning could be employed in order to facilitate higher resolution and accuracy in reading the tattoo. As an example and referring to FIG. 1, a diagram of a pH tattoo can be seen. FIG. 1 shows a round static or reference ring 10 surrounding the dynamic particle 12. The benefit of this pattern is that the static ring would provide a reliable reference if the static particles were chosen to match dynamic particle at the designated pH. For example, if the static particles were chosen to match the dynamic particle at a pH of 7.35, then the bearer of the tattoo could tell, by simple visual inspection, whether he or she was in an aerobic or anaerobic state. This would be of interest to those who work out vigorously. Since the relative color, rather than the absolute color, of the spot is the critical parameter, readings would be immune to changes in lighting conditions and skin color, since the ring would also be subject to the same changes as the dynamic spot.

Figure 2:
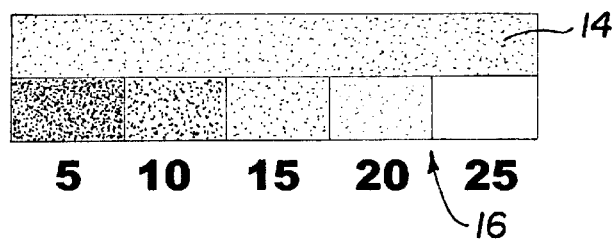
FIG. 2 is a representation of the tattoo having a non segmented static tattoo strip adjacent to a segmented dynamic tattoo strip.

FIG. 2 exhibits another format for patterning a tattoo, a segmented plus nonsegmented type. The simplest case would be a bar or strip 14 of one type adjacent or alongside a sequence of segments or strips 16 as seen in FIG. 2. If the dynariic portion of the tattoo were to change gradually over a range, then the upper bar 14 would be made from the dynamic particles and the lower segments 16 would be made from static particles. Referring to FIG. 2 it is easy to tell that the upper bar is the shade that matches 15.

Figure 3:
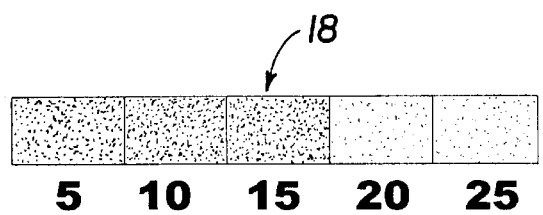
FIG. 3 is a representation of the tattoo having a segmented dynamic tattoo strip

A third case is shown in FIG. 3. Here the segments 18 have a sharp transition at different values. This configuration is more like an "on/off" switch instead of proportional. Note that it is not essential for the segments to have identical "on" state appearance.

Figure 4:
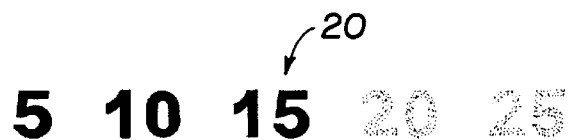
FIG. 4 is a representation of the tattoo scheme where numbers are made out of the dynamic strip.

An alternative but essentially similar scheme would be to make the numbers 20 themselves form the dynamic particles, as in FIG. 4.

Particle size may range from sub-micron to approximately 10 microns, but 1 micron is best. If the particles are too small, they will be consumed by macrophages. Particles that are too large will be ejected by scarring mechanisms A person skilled in the art of tattooing would be able to implant a suspension of the particles into the correct layer of skin, Implanting into the epidernis would cause the particles to migrate, along with epidermal cells to the surface and be worn off. Implanting the particles too deeply would initiate a scaring process that would eject the particles even if particle size were correct.

PROBE CHARACTERIZATION

To qualify as a probe, a material must change physically or chemically in response to a change in its environment This could be the analyte binding to the probe, a temperature change, a change in illumination, etc. There are two key parameters in the response of the material to the analyte which include time dependence and probe response type.

1. Time Dependence

The change may or may not be reversible, but most applications would require reversibility. If the application were cytokine or carbon monoxide sensing, the slow reversal time, hours or perhaps days, would be acceptable. In some cases such as glucose monitoring, it is desirable that the probe has a binding and releasing rate so that the overall percent of probe bound to the analyte is a function of concentration of the analyte and would follow its fluctuations with less an than hours lag.

2. Probe Response Type

Response type may be Optic and Electro-magnetic, or mechanical. Response type will dictate detection mode.

A. Optic and Electro-magnetic. This can be detected by a visible change or detectable only with sensors. Sensor types may include infrared, ultraviolet, Raman, fluorescence, microwave, NMR or EPR. Added sensitivity may be achieved in some applications by including a set of static particles in order to make readings a ratiometric type rather tan a straight intensity type.

Visible changes can be either turning dark, turning light or a color change, For example, a color change might be a pH indicator such as bromothymol blue. There are also thermochromic dyes available in a wide range of transition temperatures. The utility of visual indicators could be enhanced by several methods of reference patterns made from static particles.

B. Mechanical. Mechanical binding will alter the total mass of the particles, changing their resonant frequency and "spectral" response (absorption and reflection), thus allowing acoustic detection. A special case would be a mix of particles in which half would bind to one site on the analyte and the other half would bind to a different site. Thus, the analyte would serve to bind pairs of particles together. The spectral response shift would require minimal effort to characterize.

IMPLANTED PARTICLE CREATION

There are several methods that can produce suitable material for implantation. Ideally, particles should be the size of approximately 1 micron. Methods for this exist and the means to create such particle substrates is well understood by those skilled in the art. Particles may need to be uniform for a given type probe otherwise the particles may be sieved.

The simplest method would be the case where the probe material itself is suitable for making the particles of solid probe material. A patented case in point is carbon particles from India ink used to measure oxygen levels, as discussed in U.S. Pat. No. 5,494,030 and U.S. Pat. No. 5,706,805. The second simplest method would be to dissolve a probe in a material such as a polymer and turn the material into an appropriately sized particle by grinding and sifting, jetting, etc. A probe liquid could be mixed in another liquid in which it was immiscible. By using ultrasound to break droplets into progressively smaller sizes it is possible to get drops of probe material smaller than 1 micron. When this mixture is jetted, droplets of an appropriate size may be produced which may then be solidified. If the probe material is embedded in a porous material such as polysulfone, the resulting particles can be produced so as to have a predetermined pore size, thus allowing the analyte to come in contact with the probe, but keep the probe contained. The probe could be attached directly to the surface of the particles. Particles could be coated with a binding agent, and then the probe could be attached to the coating. The bond between the probe molecule and the particle must be strong enough to withstand the normal body processes and environmental conditions. For instance the bond should not be susceptible to hydrolization.

IMPLANTATION TECHNIQUE

The standard techniques now used in the artistic and cosmetic industries would suffice for the tattoos. For temporary tattoos, the only change would be to set the needle penetration shallow enough to ensure penetration only to the epidermis.

DETECTION METHODS

Visual methods could be used in some cases. This mode is highly desirable because of the ease of use, as no instrumentation is required. In such cases the schemes shown in FIGS. 1, 2, 3 and 4 would work well. In the simplest cases a single spot may suffice.

In the ultraviolet, visible and infrared portions of the spectrum it would be a reasonably simple matter to construct a light source and photo-detector so as to make an instrumented reading possible.

The subject of EPR detection methods is discussed in patents 5,494,030 and 5,706,805.

In the case of probes that are based on Raman or fluorescent techniques, an appropriately filtered light source and filtered detector would be used The glucose example in the prior art section identifies probe chemistry that allows for a fluorescent detection scheme.

If the particles are designed appropriately, as in the example of mechanical response, they may be able to change their ultrasound signature. This would most likely require transducers well above the 10 MHz realm, perhaps into the hundreds of MHz. Because the particles are well within he top millimeter of the surface, such higher frequencies would not be prohibited by their shallow penetration.

The subject of the invention will now be illustrated by the following examples which are not to be seen as limiting the scope in any way.

EXAMPLE 1

A pH Indicator

The first step is to select an appropriate probe molecule. Normal pH in interstitial fluid is approximately 7.35. The human survival range is about 6.8 to 8.0. The pH range used in common diagnosis of respiratory, renal and metabolic disorders is 7.00 to 7.80. Simply changing your respiratory rate can shift pH by −0.5 to +0.3.[1] A candidate probe would be bromothymol blue. The transition range for bromothymol blue is 6.0 to 7.6, with its color changing from yellow to blue. Another candidate would be phenol red, whose range is 6.8 to 8.2; however the colors are yellow to red, which may be harder to read than bromothymol blue. A competent organic chemist could perform the attachment to produce the particles. For a substrate, there are several choices, one of which is polystyrene beads. These are readily available in a 1 micron diameter. After the probe is loaded onto the surface of the beads, suspend the beads in an aqueous solution. Using standard tattooing equipment, implant the spheres to the same depth as normal tattooing ink (the dermis). When the pH in the interstitial fluid changes, the particles will change between blue and yellow. Since slight changes are of interest, it would be of use to have a tattoo that is comprised of a thick line (rather than a dot) of the active probe. Along side this, using static links, tattoo in a progression of reference segments. By observing which of these segments is the closest match to the active tattoo, a higher resolution reading of pH is possible, with higher reliability. If the person gets a little tanned, the reference tattoo is affected similarly to the active tattoo and is therefore self-recalibrating.

Guyton, A. C. and Hall, J. E.: Textbook of Medical Physiology, 9$^{th}$ Ed. Philadelphia, W. B. Saunders Company, 1996.

EXAMPLE 2

A Glucose Level Indicator

In U.S. Pat. No. 5,234,789 a method of detecting and quantizing glucose is discussed. The chemistry involved as well as detection is described in detail. Additionally, the idea of using the compounds disclosed as a tattoo ink is discussed. The molecules they refer to are far too small to effect a tattoo ink that will not be consumed by macrophages. Using the methods outlined above one could make a successful "ink" for tattooing by loading particles of appropriate size with the compounds described in the '789 Patent. Specifically, have a qualified chemist load stock polystyrene spheres with the molecule described in the '789 Patent. Suspend these particles in an aqueous solution and hire a tattoo artist to implant the particles.

EXAMPLE 3

A Temperature Indicator

Surface temperature indication has a few differences from the above examples. Firstly, there is no need to have access to interstitial fluid. This means the implant could be made temporary by placing it in the epidermal layer. In doing so, the biocompatibilty requirements are greatly reduced. Particle size is also no longer a factor, since macrophages are not present in the epidemis. This would permit using the dyes in forms not suitable for tattooing dermally.

A use for this would be for person working in cold environments where there is a real risk of frostbite. In areas that are potentially prone to this, such as fingers, temporary temperature tattoos could provide an easily read warning.

There are several sources for thermochromic dyes and inks. Among them are Spear, Inc., International Ink, CTI, Matsui International and others. Photonics magazine publishes an annual buyers' guide that has a section devoted to thermochromic materials sources. A number of these suppliers can custom make the materials to have any specified transition temperature from −25° C. to 170° C.

Other alterations and modifications of the invention will likewise become apparent to those of ordinary skill in the art upon reading the present disclosure, and it is intended that the scope of the invention disclosed herein be limited only by the broadest interpretation of the appended claims to which the inventor is legally entitled.

I claim:

1. A method of using an implantable diagnostic sensor capable of detecting a biologically relevant state or change in state of a human or animal subject, comprising:

selecting a dynamic probe material which produces a measurable change of state over a range of changes in response to a varying biologically relevant state in a human or animal subject;

selecting a reference material which exhibits a measurable state within the range of changes of the dynamic probe material that represents a desired response level of the dynamic probe material with respect to the biologically relevant state;

tattooing the dynamic probe material into the skin of the subject and tattooing the reference material for comparison next to the tattooed dynamic probe material in the skin of the subject;

comparing the state of the dynamic probe material to the state of the reference material to ascertain a biologically relevant state of the subject for which the probe was selected.

2. The method of claim 1 wherein the reference material is a single reference material which represents a desired level of response of the dynamic probe material to the biologically relevant state.

3. The method of claim 1 wherein the reference material has a color and the range of changes of the dynamic probe is a range of colors and the step of comparing the state of the dynamic probe material to the state of the reference material comprises the step of color matching to determine the biologically relevant state of the subject.

4. The method of claim 2 wherein the reference material has a color density and the range of changes of the dynamic probe is a range of color densities and the step of comparing the state of the dynamic probe material to the state of the reference material comprises the step of comparing color densities to determine the biologically relevant state of the subject.

5. The method of claim 1 wherein the step of comparing the state of the dynamic probe material to the state of the reference material is performed with the aid of an instrument.

6. The method of claim 1 wherein the reference material is segmented material which represents desired levels of responses of the dynamic probe material to the biologically relevant state.

7. The method of claim 6 wherein the reference material has a color scale and the range of changes of the dynamic probe is a range of colors and the step of comparing the state of the dynamic probe to the state of the reference material comprises matching the color of the dynamic probe with a color on the color scale of the reference probe.

8. The method of claim 6 wherein the reference material has an optical density scale and the range of changes of the dynamic probe is a range of optical density changes and the step of comparing the state of the dynamic probe to the state of the reference material is the step of matching the optical density of the dynamic probe with an optical density on the optical density scale of the reference material.

* * * * *